United States Patent [19]

Wu

[11] Patent Number: 4,570,624

[45] Date of Patent: Feb. 18, 1986

[54] UNIVERSAL GUIDE FOR INSERTING PARALLEL PINS

[75] Inventor: Kent K. Wu, Royal Oak, Mich.

[73] Assignee: Henry Ford Hospital, Detroit, Mich.

[21] Appl. No.: 521,682

[22] Filed: Aug. 10, 1983

[51] Int. Cl.⁴ .............................................. A61F 5/04
[52] U.S. Cl. ............................. 128/92 EB; 128/92 E; 128/92 A
[58] Field of Search .............. 128/92 A, 92 E, 92 EB, 128/92 R

[56] References Cited

U.S. PATENT DOCUMENTS

| | | | |
|---|---|---|---|
| 2,434,431 | 1/1948 | Pincock | 128/92 A |
| 2,725,053 | 11/1955 | Bambara et al. | 128/92 EB |
| 4,159,716 | 7/1979 | Borchers | 128/92 A |
| 4,257,411 | 3/1981 | Cho | 128/92 EB |
| 4,271,832 | 6/1981 | Evans et al. | 128/92 A |
| 4,360,012 | 11/1982 | McHarrie et al. | 128/92 A |
| 4,450,834 | 5/1984 | Fischer | 128/92 A |
| 4,502,475 | 3/1985 | Weigle et al. | 128/92 EB |

OTHER PUBLICATIONS

Machinery's Handbook, 20th ed. 1978, pp. 1947–1957, "Jigs and Fixtures".

Primary Examiner—Gene Mancene
Assistant Examiner—C. W. Shedd
Attorney, Agent, or Firm—Barnes, Kisselle, Raisch, Choate, Whittemore & Hulbert

[57] ABSTRACT

A universal guide device for drilling and inserting surgical pins which comprises an elongated bar, a plurality of blocks slideable along the bar and adapted to be adjustably locked in position on the bar. Each block supports a transverse opening, the openings in the blocks being parallel to one another. In one form a removable sleeve is provided and has a complementary external configuration corresponding to the internal configuration of the opening of each block. Each sleeve has an opening therethrough such that when the sleeves are positioned in the openings in the blocks, the openings of the sleeves are parallel to one another. Each sleeve has a serrated end for engagement with the bone of a portion of the body for holding the sleeve in position during drilling of an opening and insertion of a surgical pin.

4 Claims, 7 Drawing Figures

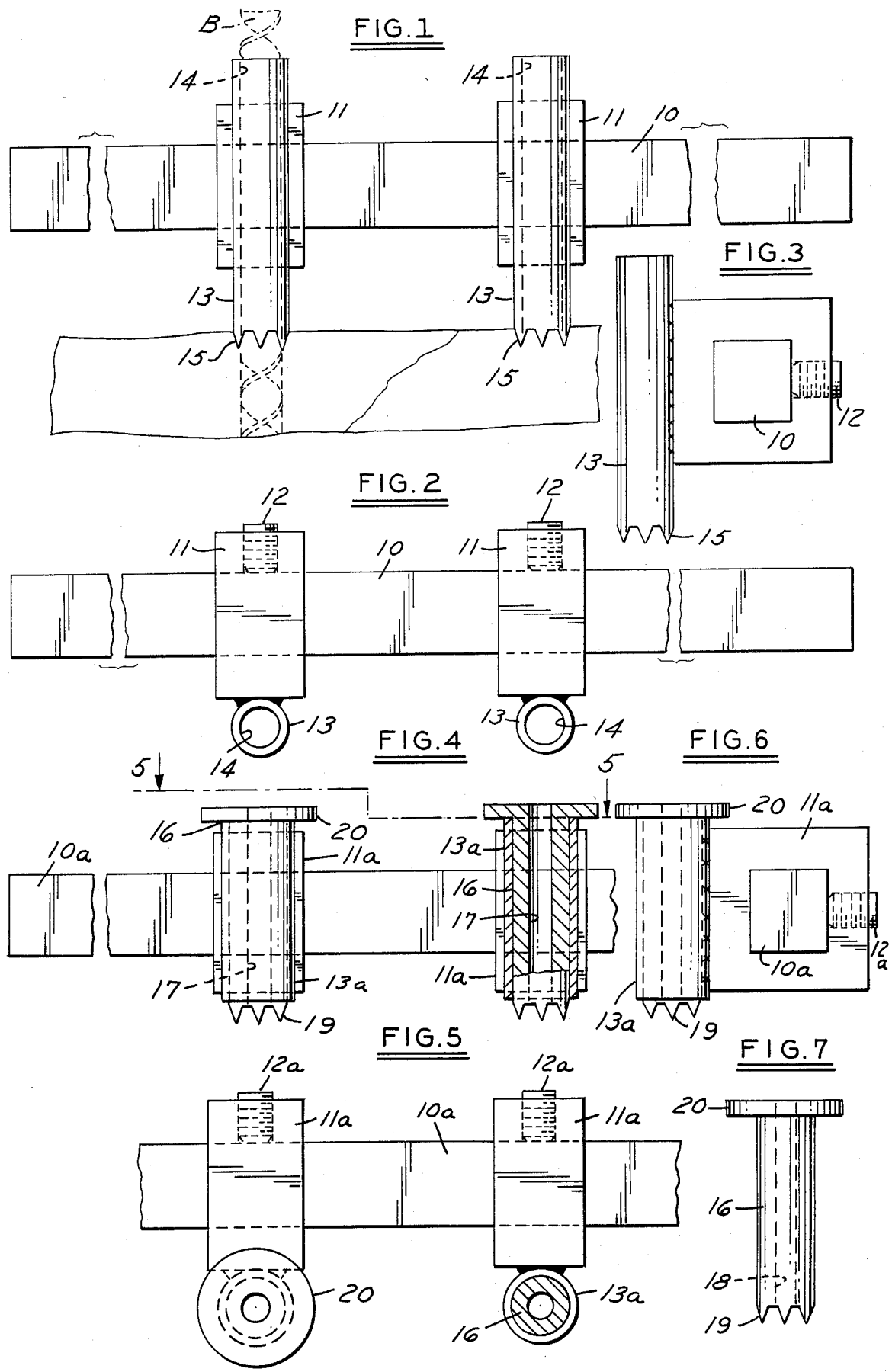

UNIVERSAL GUIDE FOR INSERTING PARALLEL PINS

This invention relates to the inserting of surgical pins such as are used in repairing fractures of bones and the like.

BACKGROUND OF THE INVENTION

In various surgical techniques such as the closed reduction of fractures of long bones or the fusion of joints, it is common to provide parallel pins through the bone portions and interconnect the pins so that the load on the limb or other part of the body is transmitted through the pins and not through the broken portions of the bone during healing. In such a procedure, it is very important that the pins be parallel to one another. Otherwise, the load is applied non-uniformly between the pins and damage may occur.

Accordingly, among the objectives of the present invention are to provide an apparatus for insuring that the pins are parallel; which can be used to fix pins at any interval or distance; which can be used for insertion of pins of various sizes, and which can be used for insertion of a large number of similar or different parallel pins.

In accordance with the invention, the apparatus comprises a plurality of blocks slideable along a bar and adapted to be adjustably locked in position on the bar. Each block supports a transverse opening, the openings in the blocks being parallel to one another. In one form each block supports serrations for engagement with a bone. In another form a removable sleeve is provided and has a complementary external configuration corresponding to the internal configuration of the opening of each block. Each sleeve has an opening therethrough such that when the sleeves are positioned in the openings in the blocks, the openings of the sleeves are parallel to one another. Each sleeve has a serrated end for engagement with the bone of a portion of the body for holding the sleeve in position during drilling of an opening and insertion of a surgical pin. Sleeves with openings of various sizes can be used to accommodate various size pins.

DESCRIPTION OF THE DRAWINGS

FIG. 1 is a partly diagrammatic view of an apparatus embodying the invention.

FIG. 2 is a fragmentary plan view of the apparatus.

FIG. 3 is an end elevational view of the apparatus.

FIG. 4 is a part sectional elevational view of a modified form of apparatus.

FIG. 5 is a fragmentary plan view taken along the line 5—5; in FIG. 4.

FIG. 6 is an end elevational view of the apparatus shown in FIGS. 4 and 5.

FIG. 7 is an elevational view of a modified insert.

DESCRIPTION

Referring to FIGS. 1-3, an apparatus embodying the invention comprises a universal guide including a bar 10 of non-circular cross section, preferably square, and a plurality of blocks 11 slideable along the length of the bar as may be required and having a set screw 12 for locking each block in adjusted position along the length of the bar 10. Each block 11 supports a fixed cylindrical sleeve 13 such that the axis of the openings 14 of the sleeves 13 are parallel to one another. The lower end of each sleeve has serrations 15 for engagement with a bone, as presently described.

In use the apparatus is brought into position adjacent a limb L and the blocks are adjusted or locked at the desired positions with the serrations 15 adjacent the limb, the other ends of the sleeves are tapped with a hammer to cause the serrations to engage the limb and hold the apparatus in position so that a drill D can be guided by openings 14 to form openings in the bone that are parallel to one another.

In the modified form of apparatus shown in FIGS. 4-7, a removable sleeve 16 having a complementary outer diameter to the internal diameter 14a of the cylinder 13a is insertable in each cylinder 13a. The sleeves 16 have different size or diameter openings 17, 18 (FIGS. 4, 5, 7) as may be required depending upon the size of the surgical pin to be inserted. Each sleeve 16 has a serrated end 19 for engagement with the bone and a flange 20 which limits the axial movement of the sleeve relative to the cylinder in one direction.

In use, the blocks 11 are adjusted to the desired position on the bar 10 and locked in position by tightening the set screws 12.

The device is then placed in position adjacent the limb as shown in FIG. 1, the sleeves 16 are tapped to cause the serrations 19 to engage the bone and hold it temporarily, a drill is inserted through the opening 17 or 18 to drill parallel holes through the spaced blocks into the bone portions. The guide is then used in a similar manner without moving it to guide the pins into the drilled openings. As a result, the surgical pins that have been inserted are parallel. Thus, when the pins are interconnected after setting the bone, they are in proper position for uniform transmission of the load on the limb during the healing process.

This form has the advantages of:
(1) Insertion of pins of all practical sizes.
(2) Fixation of pins at any intervals.
(3) A large number of similar or different parallel pins can be inserted at the same time by employing a whole series of pin guides simultaneously.

The above objectives are achieved by:
(1) Stringing and sliding the blocks of various thicknesses with attached drill guides of various diameters along the rod with a basically same cross section area which fixes these drill guides in a parallel direction.
(2) Inserting removable cylinders with central holes of various sizes to allow insertion of pins of various practical sizes.
(3) Tightening of the set screws to line up the drill guides along the bones to receive the parallel pins.
(4) Holding the drill guides in proper sites by means of their serrated ends.

The device of the invention can be used in various surgical procedures including:
(1) Closed reduction of fractures of long bones.
(2) Fusion of joints.
(3) Maintaining a constant distance when the inserted pins are interconnected to allow damaged or repaired blood vessels, nerves, tendons, ligaments, muscles, bone grafts, etc. to heal.
(4) By connecting the inserted pins with a wide variety of commercially available external fixation devices, stability of the involved area is instantly established, and the same area can be taken care of in a much more efficient manner (e.g., closer observation of wound, better drainage of infected area, easier wound care, etc.)

(5) Gradual retraction of these parallel pins allows surgical lengthening of bones previously damaged by trauma, infection, tumors and congenital anomalies.

I claim:

1. A universal guide device for drilling and inserting surgical pins which comprises
   an elongated bar having a non-circular cross section,
   a plurality of blocks having complementary non-circular openings therethrough,
   said bar extending through said non-circular openings and being slideable longitudinally on said bar,
   means for locking each said block in position on said bar,
   each said block supporting a cylindrical sleeve defining a cylindrical opening having its axis extending transversely of the longitudinal axis of the non-circular openings in said block,
   said blocks being mounted on said bar such that the cylindrical openings are parallel to one another to form guide openings for drilling openings in bone for insertion of surgical pins,
   each said cylindrical sleeve having a serrated end for engagement with the bone of a portion of the body for holding said sleeve in position during drilling of an opening and insertion of a surgical pin.

2. The universal guide set forth in claim 1 wherein said guide has a square cross section.

3. A universal guide device for drilling and inserting surgical pins which comprises
   an elongated bar having a non-circular cross section,
   a plurality of blocks having complementary non-circular openings therethrough,
   said bar extending through said non-circular openings and being slideable longitudinally on said bar,
   means for locking each said block in position on said bar,
   each said block supporting a cylinder defining a cylindrical opening having its axis extending transversely of the longitudinal axis of said bar,
   said blocks being mounted on said bar such that the cylindrical openings are parallel to one another,
   a removable cylindrical sleeve having a complementary external configuration corresponding to the internal configuration of the opening of each said cylinder of each block,
   each said sleeve having an opening therethrough such that when the sleeves are positioned in said openings in said blocks the openings of said sleeves are parallel to one another,
   each said cylindrical sleeve having a serrated end for engagement with the bone of a portion of the body for holding said sleeve in position during drilling of an opening and insertion of a surgical pin.

4. The universal guide set forth in claim 3 wherein each said sleeve includes a flange portion at the end opposite said serrated end engaging said block and limiting axial movement relative to said block in one direction.

* * * * *